United States Patent
Iselborn et al.

(10) Patent No.: US 9,346,720 B2
(45) Date of Patent: May 24, 2016

(54) ISOMERIZATION OF LIGHT ALPHA-OLEFINS TO LIGHT INTERNAL OLEFINS

(75) Inventors: Stefan Iselborn, Frankenthal (DE); Michael Hesse, Worms (DE); Piotr Makarczyk, Weisenheim am Sand (DE)

(73) Assignee: BASF SE (DE)

( * ) Notice: Subject to any disclaimer, the term of this patent is extended or adjusted under 35 U.S.C. 154(b) by 270 days.

(21) Appl. No.: 14/113,829

(22) PCT Filed: Apr. 27, 2012

(86) PCT No.: PCT/IB2012/052104
§ 371 (c)(1),
(2), (4) Date: Oct. 25, 2013

(87) PCT Pub. No.: WO2012/147047
PCT Pub. Date: Nov. 1, 2012

(65) Prior Publication Data
US 2014/0046110 A1    Feb. 13, 2014

Related U.S. Application Data

(60) Provisional application No. 61/479,869, filed on Apr. 28, 2011.

(30) Foreign Application Priority Data

Apr. 28, 2011    (EP) .................... 11164078

(51) Int. Cl.
*C07C 5/25* (2006.01)
*C07C 5/13* (2006.01)
*C07C 6/04* (2006.01)
*B01J 23/44* (2006.01)

(52) U.S. Cl.
CPC .............. *C07C 5/2512* (2013.01); *B01J 23/44* (2013.01); *C07C 5/13* (2013.01); *C07C 6/04* (2013.01); *C07C 2521/04* (2013.01); *C07C 2521/08* (2013.01); *C07C 2523/30* (2013.01); *C07C 2523/36* (2013.01); *C07C 2523/44* (2013.01); *C07C 2523/882* (2013.01); *C07C 2527/057* (2013.01); *Y02P 20/52* (2015.11)

(58) Field of Classification Search
CPC ....................................... C07C 5/25
See application file for complete search history.

(56) References Cited

U.S. PATENT DOCUMENTS

| | | |
|---|---|---|
| 3,531,545 A | 9/1970 | Garner et al. |
| 3,583,903 A | 6/1971 | Miale et al. |
| 4,166,046 A | 8/1979 | Eberly, Jr. |
| 5,087,780 A * | 2/1992 | Arganbright .............. C07C 5/05 585/259 |
| 5,502,269 A | 3/1996 | Sarrazin et al. |
| 5,877,365 A | 3/1999 | Chodorge et al. |
| 6,207,115 B1 | 3/2001 | Chodorge et al. |
| 6,211,114 B1 * | 4/2001 | Brocker ................... B01J 23/44 502/215 |
| 2002/0145226 A1 | 10/2002 | Hesse et al. |
| 2006/0235254 A1 * | 10/2006 | Gartside ............... C07C 5/2512 585/664 |
| 2008/0164138 A1 | 7/2008 | Hill et al. |
| 2008/0188703 A1 * | 8/2008 | Hill ........................ B01D 3/009 585/671 |
| 2011/0077444 A1 * | 3/2011 | Butler ...................... B01J 21/10 585/670 |

FOREIGN PATENT DOCUMENTS

| | | |
|---|---|---|
| CN | 1140749 C | 3/2004 |
| CN | 101151229 A | 3/2008 |
| EP | 0636677 A1 | 2/1995 |
| EP | 0841090 A2 | 5/1998 |
| EP | 1228803 A1 | 8/2002 |

OTHER PUBLICATIONS

International Search Report for PCT/IB2012/052104 mailed Sep. 13, 2012.
International Preliminary Report of Patentability for PCT/IB2012/052104 mailed Jul. 26, 2013.

* cited by examiner

*Primary Examiner* — In Suk Bullock
*Assistant Examiner* — Sharon Pregler
(74) *Attorney, Agent, or Firm* — Drinker Biddle & Reath LLP

(57) ABSTRACT

The present invention relates to a process for isomerizing linear alpha-olefins having from 4 to 8 carbon atoms over a heterogeneous catalyst, wherein the catalyst comprises a hydrogenation metal and a selectivity promoter selected from among selenium and tellurium on a support, and also a process for preparing 1-olefins by a metathesis reaction of 2-olefins with ethene, wherein the 2-olefins are prepared by the above mentioned isomerization process.

10 Claims, 3 Drawing Sheets

ISOMERIZATION OF LIGHT ALPHA-OLEFINS TO LIGHT INTERNAL OLEFINS

CROSS-REFERENCE TO RELATED APPLICATIONS

This application is a national stage application (under 35 U.S.C. §371) of PCT/IB2012/052104, filed Apr. 27, 2012, which claims benefit of European Application No. 11164078.5, filed Apr. 28, 2011, and U.S. Provisional Application No. 61/479,869, filed Apr. 28, 2011.

The invention relates to a process for isomerizing linear alpha-olefins having from 4 to 8 carbon atoms.

Linear alpha-olefins having from 4 to 8 carbon atoms are obtained in petrochemical processes such as catalytic or thermal cracking, pyrolysis, dimerizations, oligomerization or Fischer-Tropsch syntheses or as by-products of chemical processes, e.g. raffinates from MTBE production or BD processes. For further processing to other products, the alpha-olefins obtained in this way which have a terminal C—C double bond have to be converted by isomerization into the thermodynamically more stable linear internal olefins having the same number of carbon atoms. These internal olefins having from 4 to 8 carbon atoms can be introduced, for example, into a metathesis reaction in order to prepare other olefins, are fed to an alkylation in order to produce gasoline or are reacted in other reactions to form the desired products, for example in electrophilic additions, dimerizations, oligomerizations and copolymerizations and polymerizations.

Numerous methods of isomerizing terminal double bonds to internal double bonds in olefins are known. Such isomerization reactions can be carried out either using hydrogen, known as hydroisomerization, or without hydrogen. In both cases, an appropriate catalyst has to be used. In the absence of hydrogen, oligomerization and skeletal isomerization occur as secondary reactions. When the isomerization is carried out in the presence of hydrogen, the double bond can be hydrogenated to give saturated products. To be able to carry out hydroisomerization economically with minimal hydrogenation of the double bond, optimization and control of the reaction conditions is necessary.

Processes for isomerizing alpha-olefins are already known in principle.

U.S. Pat. No. 3,583,903 discloses a process for the transformation of hydrocarbons in the presence of a catalyst which has a molecular sieve as support and comprises sulfur, selenium or tellurium as active component. Corresponding organic reactions according to U.S. Pat. No. 3,583,903 are, for example, paraffin dehydrocyclization, isomerization and hydrocracking, olefin hydrogenation, dehydrogenation, isomerization and dehydrocyclization, naphthene dehydrogenation and dehydroisomerization, desulfurization and the like.

U.S. Pat. No. 4,166,046 discloses a process for reforming organic compounds in the presence of a catalyst which must comprise iridium as catalytically active metal. Isomerization of terminal olefins is not described in this document.

EP 1 228 803 A1 discloses a shaped core-shell catalyst body which can be used for hydrogenation, oxidation, isomerization or polymerization of organic substances. Specific organic compounds by means of which the reactions mentioned are carried out are not described in this document.

EP 0 841 090 A2 describes a catalyst which is used for the isomerization of 3-buten-1-ol compounds. The fixed-bed catalyst comprises palladium and selenium or tellurium or a mixture of selenium and tellurium on a silicon dioxide support and has a BET surface area of from 80 to 380 $m^2/g$ and a pore volume of from 0.6 to 0.95 $cm^3/g$ in the pore diameter range from 3 nm to 300 nm, with from 80 to 95% of the pore volume being in the pore diameter range from 10 to 100 nm. It is produced by impregnating a silicon dioxide support with a solution of a palladium compound and a selenium compound or tellurium compound or a mixture of a selenium compound and tellurium compound, drying the impregnated support and reducing it in the presence of hydrogen.

US2006/0235254 A1 discloses a process for isomerizing 1-butene to 2-butene in the presence of a catalyst and hydrogen. The objective of this process is to minimize the amount of butane formed as far as possible. The catalyst comprises palladium, platinum or nickel on aluminum oxide and is optionally desulfurized before the reaction.

EP 0 636 677 B1 discloses a process for isomerizing external olefins in order to obtain internal olefins. This process is carried out in the presence of a catalyst comprising palladium on a support material. The catalyst can optionally comprise from 0.05 to 10% of sulfur.

U.S. Pat. No. 3,531,545 discloses a process for isomerizing olefins in order to obtain 2-olefins. The catalyst used here comprises a noble metal on aluminum oxide. The isomerization is optionally carried out in the presence of a sulfur-comprising compound.

Disadvantages of the known processes are yields which are too low, for example as a result of secondary reactions such as branching, low selectivity and high prices of the catalysts. Furthermore, unsatisfactory activity, i.e. insufficient isomerization of the starting compounds to the desired products and excessive hydrogenation to saturated compounds, is observed in the known processes.

It is therefore an object of the present invention to provide an improved process for the isomerization, in particular hydroisomerization, of linear alpha-olefins having from 4 to 8 carbon atoms, which process displays an improved yield and selectivity to the desired products combined with reduced formation of undesirable by-products, for example saturated compounds.

These objects are achieved according to the invention by a process for isomerizing linear alpha-olefins having from 4 to 8 carbon atoms over a heterogeneous catalyst, wherein the catalyst comprises a hydrogenation metal and a selectivity promoter selected from among selenium and tellurium on a support.

Hydrogenation metals which are suitable for the purposes of the invention are, for example, palladium, platinum and/or nickel, particularly preferably palladium.

The catalyst used according to the invention has a hydrogenation metal and a selectivity promoter selected from among selenium and tellurium on a support as essential constituents. The catalyst used according to the invention thus particularly preferably comprises palladium and selenium, palladium and tellurium or palladium, selenium and tellurium, in each case on a support.

In a preferred embodiment, the support used according to the invention comprises aluminum oxide ($Al_2O_3$), silicon dioxide ($SiO_2$) or a mixture thereof.

The present invention therefore preferably provides the process of the invention in which the support comprises aluminum oxide ($Al_2O_3$), silicon dioxide ($SiO_2$) or a mixture thereof.

In a particularly preferred embodiment, the support used according to the invention consists of aluminum oxide ($Al_2O_3$) or silicon dioxide ($SiO_2$).

According to the invention, preference is given to a catalyst which comprises a hydrogenation metal or hydrogenation metals, preferably palladium and selenium or palladium and tellurium or palladium and selenium and tellurium, on a silicon dioxide or aluminum oxide support and has a BET surface area of from 20 to 400 m$^2$/g and a pore volume of from 0.2 to 0.95 cm$^3$/g in the pore diameter range from 0.001 nm to 300 µm, with from 80 to 95% of the pore volume being in the pore diameter range from 10 to 100 nm.

The BET surface area of the catalyst used according to the invention is preferably from 40 to 150 m$^2$/g, in particular from 60 to 130 m$^2$/g. The BET surface area is determined here by N$_2$ adsorption in accordance with DIN 66131.

The catalyst used according to the invention preferably comprises palladium, preferably in elemental form, as hydrogenation metal.

The present invention therefore preferably provides the process of the invention in which the hydrogenation metal is palladium, preferably in elemental form.

In general, the catalyst used according to the invention comprises palladium in an amount which allows a sufficiently high catalytic activity. For example, the catalyst used according to the invention comprises from 0.01 to 1% by weight, preferably from 0.02 to 0.8% by weight, of palladium, particularly preferably from 0.03 to 0.6% by weight, in each case based on the total weight of the catalyst and based on elemental palladium.

As selectivity promoter, the catalyst used according to the invention comprises selenium and/or tellurium, preferably in oxidic form, for example as SeO$_2$ or TeO$_2$.

The catalyst used according to the invention preferably comprises from 0.001 to 0.3% by weight, particularly preferably from 0.002 to 0.24% by weight, particularly preferably from 0.003 to 0.18% by weight, of selenium, tellurium or a mixture of selenium and tellurium, based on the total weight of the catalyst and reported as the corresponding elemental elements.

The catalyst used according to the invention particularly preferably comprises from 0.01 to 1.0% by weight, particularly preferably from 0.02 to 0.8% by weight, very particularly preferably from 0.03 to 0.6% by weight, of palladium and from 0.001 to 0.3% by weight, particularly preferably from 0.002 to 0.24% by weight, very particularly preferably from 0.003 to 0.18% by weight, of selenium, tellurium or a mixture of selenium and tellurium, preferably selenium, in each case based on the total weight of the catalyst and based on palladium, selenium and/or tellurium as the elemental elements.

Apart from the abovementioned active components, further metals can be present in small amounts on the catalyst. Preference is given to only palladium, selenium and/or tellurium, in particular only palladium and selenium, being present on the silicon dioxide or aluminum oxide support.

In a preferred embodiment of the present invention, no sulfur is present on the catalyst used according to the invention. In a further preferred embodiment of the present invention, no iridium is present on the catalyst used according to the invention. In a particularly preferred embodiment of the present invention, no sulfur and no iridium are present on the catalyst used according to the invention. Here, according to the invention means that the amounts of the specified elements are below the detection limit of the analytical methods known to those skilled in the art, for example elemental analysis.

The catalysts to be used according to the invention can generally be produced by methods known to those skilled in the art.

The elements present according to the invention on the catalyst are preferably applied by impregnation of an appropriate support with a solution of a palladium compound and a selenium compound or tellurium compound or a mixture of a selenium compound and tellurium compound. Here, it is possible to use one or more palladium compounds, selenium compounds and/or tellurium compounds. The compounds are preferably used in the form of aqueous solutions. Palladium is preferably used in the form of salts such as palladium nitrate or complexes such as tetrachloropalladate. Selenium and/or tellurium are used, for example, in oxidic form. Further suitable palladium, selenium and tellurium compounds are described in DE-A-27 51 766. Here, the support can be impregnated in succession with solutions of the individual compounds in any order, with the catalyst support being able to be dried between the individual impregnation steps. However, the catalyst support can also be impregnated with a solution comprising the compounds of the active substances in an appropriate desired ratio. The concentration of the solutions can be selected so that the desired amount of palladium and selenium and/or tellurium can be applied to the catalyst by means of a single impregnation. However, application by means of multiple impregnation is also possible.

The elements present on the support, i.e. preferably palladium and selenium, or palladium and tellurium or palladium, selenium and tellurium are preferably applied to the support in one impregnation step. This embodiment is preferred since a catalyst having an increased activity is obtained by this specific production process.

It is also possible, according to the invention, to apply palladium first and only then apply selenium and/or tellurium.

The catalyst support is preferably moved in the solution of the active substances, the impregnated catalyst is then dried at a temperature of from 80 to 160° C., for example about 120° C., and subsequently heat treated at a temperature of from 150 to 250° C., preferably about 200° C. Before or during use of the catalyst in the isomerization, the active substances, i.e. palladium and selenium and/or tellurium, are reduced in the presence of hydrogen.

In the case which is preferred according to the invention, in which silicon dioxide is used as support material, this is preferably produced by precipitating silicon dioxide from an alkali metal silicate solution, drying it and pressing it to give shaped bodies and calcining the resulting shaped bodies at a temperature in the range from 400 to 1100° C., preferably from 600 to 900° C., in particular from 800 to 900° C.

Here, for example, an aqueous ammoniacal alkali metal silicate solution is placed in a reaction vessel and treated with aqueous sulfuric acid so as to precipitate silicon dioxide. The precipitate obtained can then be filtered off, washed and spray dried. Spray drying is preferably carried out so that the silicon dioxide powder obtained has a water content which corresponds to a loss on ignition of from 25 to 35% by weight on ignition at 900° C. for 2 hours. The silicon dioxide powder obtained can then be mixed with a peptizing agent to form a paste and brought to the desired shape. When the catalyst is used as fixed-bed catalyst, it can have all suitable macroscopic shapes, for example the shape of extrudates, tablets, pellets of any shape, spheres or rings. Preference is given to pressing the silicon dioxide powder to form extrudates. The extrudates are then dried at from 120 to 150° C. and subsequently calcined at from 400 to 1100° C., preferably from 600 to 900° C., in particular from 800 to 900° C.

Other methods of producing the silicon dioxide support which is preferred according to the invention can be chosen as long as the supports obtained have the indicated BET surface area, pore size and pore size distribution.

In the further preferred case in which aluminum oxide is used as support material, this is preferably produced by peptizing a suitable aluminum-comprising raw material, preferably boehmite, by means of a peptizing agent such as water, dilute acid or dilute base. As acid, use is made of, for example, a mineral acid such as nitric acid or an organic acid such as formic acid. As base, preference is given to using an inorganic base such as ammonia. The acid or base is generally dissolved in water. Water or dilute aqueous nitric acid are preferably used as peptizing agent. The concentration of the nonaqueous fraction in the peptizing agent is generally from 0 to 10% by weight, preferably from 0 to 7% by weight, particularly preferably from 0 to 5% by weight. After peptization, the support is shaped, dried and calcined.

Boehmite ($\gamma$-AlO(OH)) is a widely available commercial product, but can also be prepared in a known way by precipitation from a solution of an aluminum salt, for example aluminum nitrate, by means of a base, isolation, washing, drying and calcination of the precipitated solid immediately before the actual production of the support.

Boehmite is advantageously used in the form of a powder. A suitable commercial boehmite powder is, for example, Versal® 250, which can be obtained from UOP. The boehmite is treated with the peptizing agent by moistening and intensively mixing it with the peptizing agent, for example in a kneader, mixer or pan mill. Peptization is continued until the composition can readily be shaped. The composition is subsequently shaped by means of conventional methods to give the desired shaped support bodies, for example by ram extrusion, screw extrusion, tableting or agglomeration. Any known method is suitable for shaping. If necessary or advantageous, customary additives can be used. Examples of such additives are extrusion or tableting aids such as polyglycols or graphite.

It is also possible to mix additives which influence the pore structure of the support after calcination in a known way as burn-out materials, for example polymers, fibrous materials, natural burn-out materials such as ground nutshells, or other customary additives with the raw support composition before shaping. Preference is given to the use of boehmite in a particle size distribution and the addition of burn-out materials which leads to a pore radius distribution of the finished support in which from 50 to 90% by volume of the total pore volume is present in the form of pores having an average diameter in the range from 0.01 to 0.1 µm and from 10 to 50% by volume of the total pore volume is present in the form of pores having an average diameter in the range from 0.1 to 1 µm. The measures necessary for this purpose are known per se to those skilled in the art.

After shaping, the shaped bodies are dried in a conventional way, generally at a temperature above 60° C., preferably above 80° C., particularly preferably above 100° C., very particularly preferably at a temperature in the range from 120 to 300° C. Drying is continued until water present in the shaped bodies has been given off essentially completely from the shaped bodies, which is generally the case after a few hours. Customary drying times are in the range from 1 to 30 hours and are dependent on the drying temperature set, with a higher temperature shortening the drying time. Drying can be accelerated further by use of subatmospheric pressure.

After drying, the shaped bodies are converted into the finished support by calcination. The calcination temperature is generally in the range from 400 to 1150° C. The calcination time is generally in the range from 0.5 to 5 hours, preferably from 1 to 4 hours, particularly preferably from 1.5 to 3 hours. Calcination is carried out in a conventional furnace, for example in a rotary furnace, in a tunnel kiln, in a belt calciner or in a chamber furnace. The calcination can follow drying directly without intermediate cooling of the shaped bodies.

In a particularly preferred embodiment, the catalyst is used as fixed-bed catalyst.

Reactor

The isomerization of the invention can be carried out in any apparatus in which it is possible to carry out a continuous process. The isomerization is preferably carried out in the downflow mode in a tube reactor comprising the fixed-bed catalyst to be used according to the invention. The tube reactor preferably comprises a gas distributor, for example in the form of a filter plate, a static mixer or a nozzle, in the upper part. The gas distributor serves to introduce gas mixture, for example hydrogen/nitrogen, so that the reactor cross section is preferably uniformly supplied with gas. The compound to be isomerized is firstly conveyed through a heating zone, mixed with the gas and fed into the reactor. The space velocity over the catalyst is set so that a conversion of the olefin at the reactor outlet of preferably from 30 to 100%, particularly preferably from 50 to 100%, very particularly preferably from 50 to 90%, is achieved.

The process of the invention is preferably carried out in the presence of hydrogen. In this preferred embodiment, the introduction of hydrogen is set as a function of temperature and total pressure so that a hydrogen partial pressure of from 0.1 to 25 bar, preferably from 5 to 20 bar, in particular from 5 to 12 bar, is maintained. The hydrogen passed through the reactor can, in the reactor output, be discharged as offgas after condensing out low boilers or be recirculated to the process. In a further preferred embodiment, the process of the invention is carried out in the presence of an inert gas, for example nitrogen or methane.

Process Parameters

The isomerization is preferably carried out at a pressure of from 4 to 35 bar absolute, in particular from 5 to 25 bar absolute.

The isomerization is generally carried out at temperatures in the range from 10 to 150° C., preferably from 30 to 120° C., for example from 50 to 100° C. According to the invention, space velocities over the catalyst of from 0.5 to 15 kg/l (catalyst)×h, preferably from 1 to 10 l/l (catalyst)×h, are generally employed, depending on the starting compound used.

The present invention therefore preferably provides the process of the invention in which the isomerization is carried out at a temperature of from 30 to 120° C.

In a preferred embodiment, the isomerization is carried out in the presence of hydrogen. The present invention therefore preferably provides the process of the invention carried out in the presence of hydrogen.

In a further preferred embodiment, the isomerization is carried out in the presence of a mixture of hydrogen and inert gas, preferably methane or nitrogen. In a very particularly preferred embodiment, the inert gas used in the isomerization is methane, with the hydrogen used being used in a relative proportion by volume of from 80 to 98 mol % based on the total amount of hydrogen and methane gas.

In a particularly preferred embodiment, the process of the invention for isomerizing olefins is carried out in the absence of carbon monoxide. For the purposes of the present invention, "in the absence of carbon monoxide" means that carbon monoxide is present in a maximum amount of 1 ppm by weight in the reaction mixture.

In a particularly preferred embodiment, the process of the invention for isomerizing olefins is carried out in the absence of sulfur-comprising compounds. For the purposes of the present invention, "in the absence of sulfur-comprising compounds" means that sulfur-comprising compounds are present in a maximum amount of less than 1 ppm by weight in the reaction mixture.

In a further preferred embodiment, the process of the invention for isomerizing olefins is carried out without sulfurization of the catalyst having been carried out beforehand. In a preferred embodiment, the catalyst is introduced into the reactor after production of the catalyst and the isomerization is commenced immediately by feeding in the appropriate substrates.

The process of the invention can be carried out in the presence or absence of an inert organic solvent. Inert organic solvents which can be used are, for example, ethers such as diethyl ether, dioxane, tetrahydrofuran, alcohols such as ethanol, isobutanol, aromatic or aliphatic hydrocarbons such as n-hexane, heptane or benzene or mixtures thereof.

The hydroisomerization, i.e. the process of the invention in the presence of hydrogen, can be accompanied by hydrogenation. This embodiment is, for example, preferred when the reaction mixture also comprises acetylenes, for example butyne and/or vinylacetylene, or dienes, for example butadiene, so that these are hydrogenated in the presence of the isomerization catalyst.

The process of the invention is preferably carried out together with a selective hydrogenation of acetylenes or diolefins. The hydrogenation of acetylenes, for example butyne and/or vinylacetylene, and/or butadiene preferably forms 1-butene which is then isomerized to 2-butene by the process of the invention.

Starting Materials

The linear alpha-olefins having from 4 to 8 carbon atoms which are to be isomerized according to the invention can be present as uniform compounds or as a mixture of alpha-olefins having different chain lengths ranging from four carbon atoms to eight carbon atoms.

Examples of linear alpha-olefins used according to the invention as substrates are 1-n-butene, 1-n-pentene, 1-n-hexene, 1-n-heptene or 1-n-octene. The linear alpha-olefins having from 4 to 8 carbon atoms which are used according to the invention can be used as individual compounds or as a mixture of a plurality of the compounds mentioned. Further organic compounds, for example olefins having two or more double bonds and from 4 to 8 carbon atoms, for example butadiene, can optionally also be present in the reaction mixture. In the presence of compounds having two or more double bonds, for example acetylenes, all but one are selectively hydrogenated by means of the preferred presence of hydrogen in a preferred embodiment of the process of the invention, so that the corresponding alpha-olefins are preferably formed and are then likewise converted according to the invention into the corresponding internal olefins.

In the isomerization of the invention, the double bond present in the molecule is generally shifted from the 1 position, i.e. the alpha position, to an internal position. Depending on the number of carbon atoms in the substrate, various internal positions are possible according to the invention. 1-Butene can, for example, be isomerized to 2-butene. 1-Pentene can be isomerized to 2-pentene. 1-Hexene can be isomerized to 2- and/or 3-hexene, etc.

In the process of the invention, the 1-olefins used are preferably converted into the corresponding 2-olefins, i.e. the double bond is preferably shifted from the 1 position to the 2 position in the isomerization of the invention.

The 2-olefins which are preferably formed according to the invention can, depending on their chain length, be obtained as cis and/or trans isomers.

Particular preference is given to 1-pentene being isomerized to cis- and/or trans-2-pentene in the process of the invention. In a further preferred embodiment, 1-butene is isomerized to cis- and/or trans-2-butene by the process of the invention.

The olefins which have been isomerized according to the invention, preferably linear 2-olefins, are suitable, for example, for preparing propene by metathesis with appropriate further olefins. The internal olefins are also required, for example, for the production of gasoline by alkylation or for reactions with other reagents in electrophilic additions such as halogenation, water addition or dimerizations, oligomerizations and polymerizations, for example free-radical reactions of the internal olefins.

The present invention therefore further provides a process for preparing 1-olefins, for example propene, by a metathesis reaction of 2-olefins with ethene, wherein the 2-olefins are prepared by the isomerization process of the invention.

In a preferred embodiment, the present invention provides the metathesis process of the invention in which ethene is reacted with 2-butene to form propene. As a result of the 2-olefins, preferably 2-butene, required being obtainable in a particularly high purity in the process of the invention, the corresponding products, preferably propene, can be prepared in a particularly high yield and selectivity by the metathesis process of the invention.

Processes for the metathesis of olefins are known per se to those skilled in the art and are described, for example, in K. Weissermel, H.-J. Arpe, "Industrielle organische Chemie", fifth edition, Wiley VCH 1998, chapter 3.4 Olefin-Metathese, pages 95 to 99. As catalysts, it is possible to use, for example, metal-organic catalysts of the Schrock or Grubbs type.

The present invention therefore also provides the metathesis process of the invention in which the metathesis is carried out in the presence of a catalyst comprising $WO_3/SiO_2$, $CoO-MoO_3/Al_2O_3$, $Re_2O_7/Al_2O_3$ or other typical metathesis catalysts.

BRIEF DESCRIPTION OF THE FIGURES

FIG. 1 shows the selectivity (S) to 2-pentene in percent relative to the conversion of 1-pentene (P) in percent. The graphs relate to:

| | |
|---|---|
| Diamond | Catalyst A |
| Square | Catalyst B |
| Triangle | Catalyst C |

Figure 2:
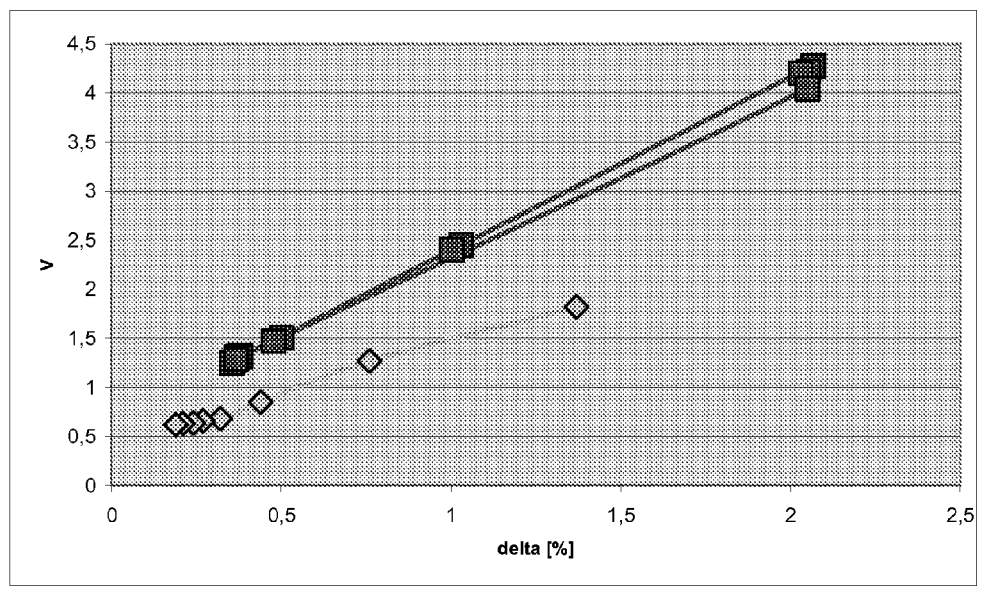

FIG. 2 shows the ratio (R) of 2-butene to 1-butene versus delta butane (delta) in percent. The graphs relate to:

| | |
|---|---|
| Diamond | Catalyst A, 60° C. |
| Square | Catalyst C, 60° C. |

Figure 3:
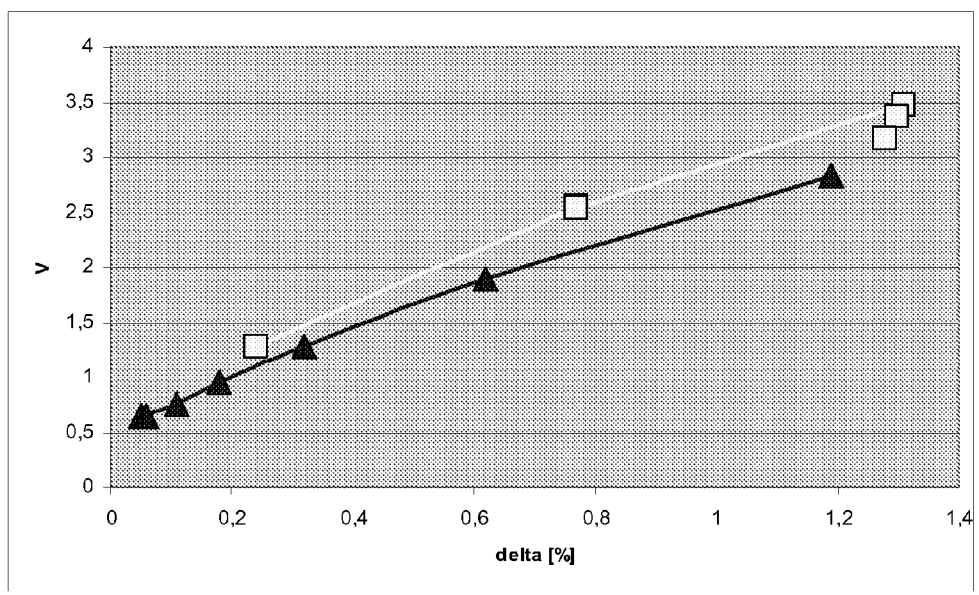

FIG. 3 shows the ratio (R) of 2-butene to 1-butene versus delta butane (delta) in percent. The graphs relate to:

| | |
|---|---|
| Diamond | Catalyst A, 80° C. |
| Square | Catalyst C, 80° C. |

EXAMPLES

1. Production of the Catalysts

1.1 Catalyst A (Comparison)

Catalyst A is a commercially available catalyst comprising 0.3% by weight of Pd on an aluminum oxide support.

1.2 Catalyst B (According to the Invention)

Catalyst B is produced by applying the isomerization promoter $SeO_2$ to catalyst A by means of spray impregnation. The spray impregnation process is known to those skilled in the art. The amount of impregnation solution is set at 95% of the water uptake of the support and the concentration of the isomerization promoter $SeO_2$ in the impregnation solution is calculated so as to give a 0.042% by weight loading of $SeO_2$ in the finished catalyst. The impregnated catalyst is heated to 120° C. over a period of 90 minutes in 100 standard l of air per 100 g of catalyst per hour and dried at this temperature under the same stream of air for 180 minutes. The dry catalyst is heated to 200° C. over a period of 60 minutes and calcined at this temperature under the same stream of air for 180 minutes.

1.3 Catalyst C (According to the Invention)

An aqueous ammoniacal sodium silicate solution is placed in a stirred vessel. Silicon dioxide is precipitated by means of aqueous sulfuric acid while stirring. The precipitate obtained is filtered off, washed and subsequently spray dried. Spray drying is carried out so that the silicon dioxide powder obtained has a water content corresponding to a loss on ignition in the range from 25 to 35% by weight in 2 hours at 900° C. The silicon dioxide powder obtained in this way is mixed with water and ammonia as peptizing agent to give a paste and pressed to give extrudates having a diameter of 3 mm. The extrudates are dried at from 120 to 150° C. in a drying oven and subsequently calcined at from 820 to 870° C.

300 g of the resulting support material in the form of extrudates having a diameter of 3 mm are admixed with an aqueous solution composed of 13.64 g of palladium nitrate solution comprising 11% by weight of palladium and 0.21 g of $SeO_2$ in 244 g of distilled water in a round-bottom flask on a rotary evaporator. The flask is rotated at room temperature until the entire solution has been taken up by the support material. While rotating the flask, the flask with the catalyst is subsequently heated to 120° C. and dried at a speed of rotation of 9 revolutions per minute for 3 hours while passing 2000 l of air per hour through the flask. After drying, the temperature is increased to 200° C. while continuing to rotate the flask and passing 1000 l of air/h through the flask and the catalyst is heat treated for 3 hours.

The silicon dioxide supported catalyst obtained in this way comprises 0.5% by weight of palladium and 0.05% by weight of selenium, based on the total weight of the catalyst. The BET surface area is 119 $m^2/g$ and the pore volume in the pore diameter range from 3 nm to 300 μm is 0.82 $cm^3/g$. Of this pore volume, 91.7% is in the pore diameter range from 10 to 100 nm.

2. Experiments on the Isomerization of 1-pentene

2.1 Experiment 1 (Comparison)

3 g of catalyst A are placed in a catalyst basket in a 250 ml autoclave. The catalyst is reduced under a stream of $H_2$ at 120° C. for 2 hours. After the autoclave has cooled, 150 g of a 20% strength solution of 1-pentene in n-hexane are introduced into the autoclave. After closing the reactor, it is pressurized with hydrogen to 1.5 bar and heated to a temperature of 30° C. The stirrer is set to 1000 rpm and samples are taken every 15 minutes and analyzed by means of GC.

2.2 Experiment 2 (According to the Invention)

The experiment is carried out in a manner analogous to experiment 1 (2.1) except that catalyst B is used instead of catalyst A.

2.3 Experiment 3 (According to the Invention)

The experiment is carried out in a manner analogous to experiment 1 (2.1) except that catalyst C is used instead of catalyst A.

2.4 Results and Evaluation

Figure 1:
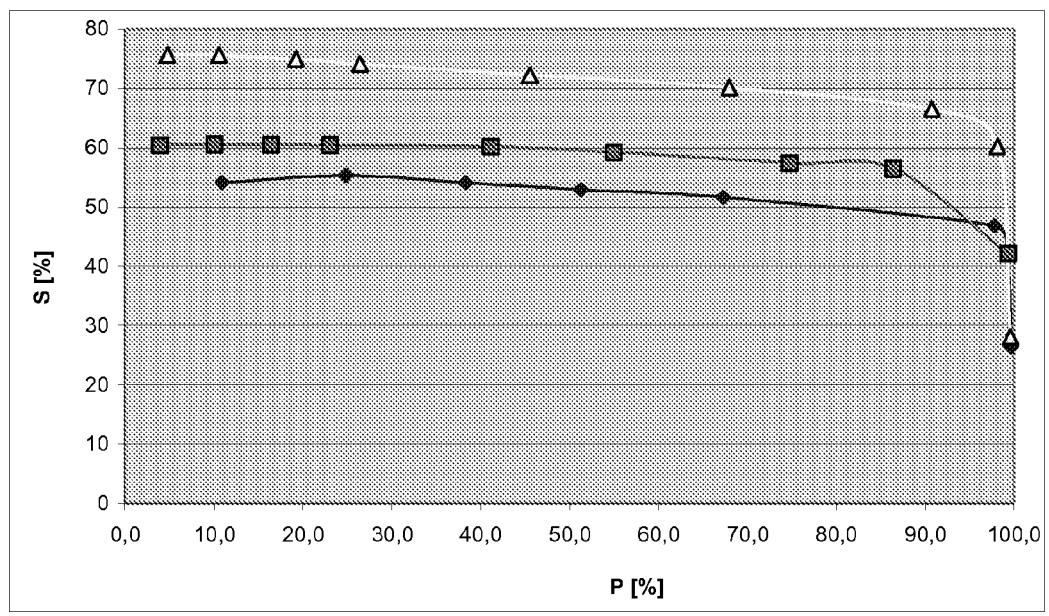
FIGS. 1, 2 and 3 show the following.

The results of the three experiments are shown in table 1 and FIG. 1.

The selectivities to 2-pentenes are calculated using the following formula:

$$\text{Selectivity} = \text{concentration of 2-pentenes} * 100 / \text{concentration of the sum of pentane and 2-pentenes}$$

As can be seen from table 1 and FIG. 1, the catalysts B and C according to the invention achieve up to 20% higher selectivities to 2-pentenes in a hydroisomerization of 1-pentene in the liquid phase than the comparative catalyst A.

TABLE 1

| 1-Pentene Vol-% | trans-2-Pentene Vol-% | cis-2-Pentene Vol-% | Sum of 2-pentenes Vol-% | Pentane Vol-% | Duration of experiment Minutes | Selectivity to 2-pentenes % | Conversion % |
|---|---|---|---|---|---|---|---|
| Catalyst A |||||||||
| 19.9 | 0.0 | 0.0 | 0.0 | 0.0 | 0.0 | | |
| 17.7 | 0.6 | 0.5 | 1.1 | 0.9 | 15.0 | 54.1 | 10.9 |
| 15.0 | 1.3 | 1.1 | 2.4 | 2.0 | 30.0 | 55.4 | 24.9 |
| 12.3 | 2.0 | 1.7 | 3.7 | 3.2 | 45.0 | 54.1 | 38.3 |
| 9.7 | 2.6 | 2.1 | 4.7 | 4.2 | 60.0 | 52.9 | 51.3 |
| 6.5 | 3.9 | 3.0 | 6.8 | 6.4 | 90.0 | 51.6 | 67.3 |
| 0.4 | 4.5 | 2.4 | 6.9 | 7.9 | 150.0 | 46.8 | 97.8 |
| 0.2 | 6.0 | 2.3 | 8.3 | 11.3 | 180.0 | 42.2 | 99.2 |
| 0.1 | 4.2 | 0.9 | 5.1 | 14.2 | 300.0 | 26.3 | 99.7 |
| Catalyst B |||||||||
| 19.8 | 0.0 | 0.0 | 0.0 | 0.0 | 0.0 | | |
| 19.0 | 0.2 | 0.2 | 0.4 | 0.3 | 15.0 | 60.4 | 4.0 |
| 17.8 | 0.7 | 0.5 | 1.1 | 0.7 | 30.0 | 60.6 | 10.1 |
| 16.5 | 1.2 | 0.8 | 2.0 | 1.3 | 45.0 | 60.5 | 16.5 |
| 15.2 | 1.7 | 1.1 | 2.8 | 1.8 | 60.0 | 60.5 | 23.1 |
| 11.7 | 2.4 | 1.6 | 4.0 | 2.7 | 90.0 | 60.2 | 41.2 |
| 8.9 | 3.9 | 2.5 | 6.4 | 4.4 | 120.0 | 59.2 | 55.0 |
| 5.0 | 5.4 | 3.1 | 8.5 | 6.3 | 150.0 | 57.4 | 74.8 |
| 2.7 | 6.4 | 3.2 | 9.6 | 7.4 | 180.0 | 56.5 | 86.4 |
| 0.1 | 6.6 | 1.6 | 8.2 | 11.3 | 300.0 | 42.1 | 99.4 |

TABLE 1-continued

| 1-Pentene Vol-% | trans-2-Pentene Vol-% | cis-2-Pentene Vol-% | Sum of 2-pentenes Vol-% | Pentane Vol-% | Duration of experiment Minutes | Selectivity to 2-pentenes % | Conversion % |
|---|---|---|---|---|---|---|---|
| \multicolumn{8}{c}{Catalyst C} | | | | | | | |
| 19.9 | 0.0 | 0.0 | 0.0 | 0.0 | 0.0 | | |
| 18.9 | 0.4 | 0.3 | 0.7 | 0.2 | 15.0 | 75.6 | 4.8 |
| 17.8 | 1.0 | 0.6 | 1.6 | 0.5 | 30.0 | 75.6 | 10.6 |
| 16.1 | 1.7 | 1.0 | 2.7 | 0.9 | 45.0 | 74.9 | 19.2 |
| 14.6 | 2.5 | 1.4 | 3.9 | 1.4 | 60.0 | 74.1 | 26.4 |
| 10.8 | 4.2 | 2.3 | 6.5 | 2.5 | 90.0 | 72.3 | 45.5 |
| 6.4 | 6.3 | 3.2 | 9.5 | 4.0 | 120.0 | 70.1 | 67.9 |
| 1.8 | 7.8 | 3.3 | 11.1 | 5.6 | 150.0 | 66.5 | 90.8 |
| 0.4 | 9.0 | 2.7 | 11.8 | 7.8 | 180.0 | 60.2 | 98.2 |
| 0.1 | 4.5 | 1.0 | 5.5 | 14.2 | 300.0 | 28.0 | 99.6 |

3. Experiments on the Selective Hydrogenation of 1,3-Butadiene (BD for Short) to n-Butene with Hydroisomerization of 1-Butene to 2-Butene The experiments on C4 hydrogenation are carried out in a fixed bed reactor with circulation and separator. After installation, the catalyst is reduced under a stream of hydrogen at a pressure of 5 bar (g) for 12 hours. As substrate stream (feed), use is made of raffinate I after hydrogenation comprising 0.5-0.7% by volume of butadiene and having a ratio of 2-butene to 1-butene of 0.6.

The reaction conditions are as follows:

| | |
|---|---|
| whsv [kg/l/h] | 8.5 |
| Recycle to feed ratio | 1.9 |
| Cross-sectional loading [m$^3$/m$^2$/h] | 39 |
| Pressure | Vapor pressure of the hydrogenated product (no offgas 7-8 bar) |
| Temperature | 60° C. and 80° C. |

In the experiments, the molar ratio of H$_2$/BD in the substrate stream is varied from 2:1 to 6:1 (mol/mol), while all other parameters remain unchanged, i.e. complete conversion of BD is achieved in all experiments.

The composition of the product obtained is evaluated in respect of the ratio of 2-butenes to 1-butene and in respect of the formation of butane (n-Bu). "Delta butane" is calculated from the concentration of butane at the reactor outlet minus the concentration of butane in the substrate stream (feed). The results are shown in table 2 and FIGS. 2 and 3:

TABLE 2

| | 2-Bu/1-Bu | | |
|---|---|---|---|
| n-Bu Formation | 40° C. | 60° C. | 80° C. |
| \multicolumn{4}{c}{Catalyst A} | | | |
| 1.67 | 1.18 | — | — |
| 1.03 | 0.85 | — | — |
| 0.77 | 0.74 | — | — |
| 0.66 | 0.69 | — | — |
| 0.61 | 0.67 | — | — |
| 0.59 | 0.66 | — | — |
| 0.55 | 0.65 | — | — |
| 0.3 | 0.65 | — | — |
| 1.37 | — | 1.82 | — |
| 0.76 | — | 1.27 | — |
| 0.44 | — | 0.85 | — |
| 0.32 | — | 0.68 | — |
| 0.27 | — | 0.66 | — |
| 0.24 | — | 0.64 | — |
| 0.21 | — | 0.63 | — |
| 0.19 | — | 0.62 | — |
| 1.19 | — | — | 2.83 |
| 0.62 | — | — | 1.89 |
| 0.32 | — | — | 1.28 |
| 0.18 | — | — | 0.95 |
| 0.11 | — | — | 0.76 |
| 0.05 | — | — | 0.65 |
| 0.06 | — | — | 0.64 |
| 0.06 | — | — | 0.64 |
| \multicolumn{4}{c}{Catalyst C} | | | |
| 0.50 | — | 1.50 | — |
| 0.48 | — | 1.47 | — |
| 1.03 | — | 2.45 | — |
| 1.00 | — | 2.40 | — |
| 2.07 | — | 4.28 | — |
| 2.05 | — | 4.22 | — |
| 2.03 | — | 4.20 | — |
| 2.05 | — | 4.05 | — |
| 0.38 | — | 1.31 | — |
| 0.36 | — | 1.25 | — |
| 0.37 | — | 1.31 | — |
| 0.38 | — | 1.32 | — |
| 0.37 | — | 1.31 | — |
| 0.37 | — | 1.30 | — |
| 0.37 | — | 1.29 | — |
| 0.24 | — | — | 1.274 |
| 0.24 | — | — | 1.28 |
| 0.77 | — | — | 2.56 |
| 0.77 | — | — | 2.54 |
| 1.31 | — | — | 3.48 |
| 1.3 | — | — | 3.37 |
| 1.28 | — | — | 3.17 |

In table 2 and FIGS. 2 and 3, a significantly higher isomerization of 1-butene can be observed when using catalyst C in the process of the invention than in the comparative experiment (catalyst A). At the same time, lower overhydrogenation is found when using catalyst C than in the comparative experiment (catalyst A).

4. Metathesis Reaction 4.1 Production of Catalyst for the Metathesis Reaction:

Part A: 235.2 g of SiO$_2$ extrudates (BASF) having a diameter of 1.5 mm are impregnated to the water uptake with an aqueous solution composed of 30.9 g of ammonium metatungstate and 635 g of water. After 15 minutes, the extrudates are predried at 80° C. and 50 mbar on a rotary evaporator, then dried overnight at 120° C. in a vacuum drying oven and finally calcined at 600° C. in a stream of N$_2$.

Part B: 400 g of Al$_2$O$_3$ extrudates (BASF) having a diameter of 1.5 mm are impregnated to the water uptake with an aqueous solution of 368.9 g of magnesium nitrate hexahydrate and 8.1 g of sodium nitrate made up to 281 ml. The extrudates are dried overnight at 120° C. in a drying oven and subsequently calcined at 500° C. in a stream of $N_2$.

4.2 Use of the Catalyst from Example 4.1 in the Metathesis Reaction:

20 g of catalyst as a mixture of 5 g of catalyst as per example 4.1, part A, and 15 g of catalyst as per example 4.1, part B, in the form of 1.5 mm extrudates are installed in a tube reactor. The catalyst is activated by passing air over it at 600° C., blanketing it with a stream of $N_2$ while cooling to 530° C. and passing a raffinate stream over it while cooling to the reaction temperature. The feed for the metathesis comprises ethylene and a butene mixture. As butene mixture, use is made of a mixture of about 85% by weight of linear butenes, about 2.5% by weight of isobutene and butanes (balance to 100% by weight) from example 3 using comparative catalyst A or a corresponding mixture from example 3 using catalyst C according to the invention.

The reaction is carried out at 300° C. and 25 bar. The inlet and outlet compositions are determined by means of on-line GC. Conversions and mass selectivities for the metathesis are determined therefrom for the two experiments with different 2-butene/1-butene ratios in the substrate. The mass selectivity here indicates the proportion by mass of propene in the product (propene plus olefins of C5 and above).

It can be seen that more propylene is also formed when there is a higher proportion of 2-butene in the feed, i.e. substrate stream from example 3 using catalyst C according to the invention, which shows up in an increase in the butene conversion and the propene selectivity in this experiment with a higher proportion of 2-butene in the feed.

The invention claimed is:

1. A process for isomerizing linear alpha-olefins having from 4 to 8 carbon atoms over a heterogeneous catalyst, wherein the catalyst comprises a hydrogenation metal selected from the group consisting of palladium, platinum, nickels, and mixtures thereof, and a selectivity promoter selected from the group consisting of selenium and tellurium on a support, wherein the isomerization is carried out at a temperature of from 30 to 120° C.

2. The process according to claim 1 carried out in the presence of hydrogen.

3. The process according to claim 1, wherein the support comprises aluminum oxide ($Al_2O_3$), silicon dioxide ($SiO_2$) or a mixture thereof.

4. The process according to claim 1, wherein a catalyst which comprises palladium and selenium or tellurium, on a support has a surface area of from 80 to 380 $m^2/g$, a pore volume of from 0.6 to 0.95 $cm^3/g$ and a pore diameter of from 3 nm to 300 μm, with from 80 to 95% of the pore volume being in the pore diameter range from 10 to 100 nm, is used.

5. The process according to claim 1, wherein the catalyst comprises from 0.1 to 0.8% by weight of palladium, from 0.02 to 0.08% by weight of selenium, tellurium or a mixture of selenium and tellurium, based on the total weight of the catalyst.

6. The process according to claim 1, wherein the isomerization is carried out at a pressure of from 4 to 35 bar.

7. The process according to claim 1, wherein the hydrogenation metal is palladium.

8. The process according to claim 7, wherein the palladium is in elemental form.

9. A process comprising:
   a. preparing a 2-olefin by the process according to claim 1; and
   b. preparing a 1-olefin reacting the 2-olefin with ethane in a metathesis reaction.

10. The process according to claim 9, wherein the metathesis is carried out in the presence of a catalyst selected from the group consisting of $WO_3/SiO_2$, $CoO$—$MoO_3/Al_2O_3$, $Re_2O_7/Al_2O_3$ and mixtures thereof, or metal-organic catalysts of the Schrock or Grubbs type.

* * * * *